United States Patent [19]

Bowen

[11] Patent Number: 5,320,886
[45] Date of Patent: Jun. 14, 1994

[54] HYDROPHILIC CROSSLINKING MONOMERS AND POLYMERS MADE THEREFROM

[75] Inventor: Rafael L. Bowen, Gaithersburg, Md.

[73] Assignee: American Dental Association Health Foundation, Gaithersburg, Md.

[21] Appl. No.: 791,999

[22] Filed: Nov. 14, 1991

[51] Int. Cl.$^5$ .................... B29D 22/00; A61K 6/08; C08G 69/00

[52] U.S. Cl. .................................. 428/34.1; 528/126; 528/127; 528/173; 528/179; 528/182; 528/185; 528/188; 528/205; 528/222; 528/223; 528/224; 528/332; 528/336; 528/337; 528/344; 528/345; 525/42; 525/43; 523/116

[58] Field of Search .................. 428/34.1; 525/42, 43; 528/126, 127, 173, 179, 182, 185, 188, 205, 222, 223, 224, 332, 336, 337, 344, 345; 523/116

[56] References Cited

U.S. PATENT DOCUMENTS

| | | |
|---|---|---|
| 3,066,112 | 11/1962 | Bowen . |
| 3,194,783 | 7/1965 | Bowen . |
| 4,224,023 | 9/1980 | Cheung . |
| 4,514,527 | 4/1985 | Bowen . |
| 4,521,550 | 6/1985 | Bowen . |
| 4,588,756 | 5/1986 | Bowen . |
| 4,659,751 | 4/1987 | Bowen . |

OTHER PUBLICATIONS

Dental Adhesives, p. 2, May 1990, Reality Publishing Company, Houston, Tex.

*Primary Examiner*—John Kight, III
*Assistant Examiner*—Dvc Truong
*Attorney, Agent, or Firm*—Allegretti & Witcoff, Ltd.

[57] ABSTRACT

This invention relates primarily to organofunctional monomers, predominantly dimethacrylates and/or diacrylates containing one or more (predominantly two carboxyl groups, with moieties that provide sufficient affinity with water to allow any desired amount of water and/or miscible fugitive solvents to be mixed homogeneously with these monomers and formulations containing them. The activity of water in the monomer formulations can be adjusted so that it is equal to the water activity in biological tissues. This promotes biocompatibility and enhances the adhesive characteristics of polymers prepared from these formulations. Probability statistics are disclosed that optimize the compositions of polymer reaction products. Also disclosed are novel, dual-purpose synthesis reaction monomers, catalysts, stabilizers, polymerization initiators and/or cophotoinitiators that have solubility and surface-activity characteristics such that they will not become separated by partitioning during penetration of hydrated layers on or in the substrate adherends. These formulations may be used for light-cured or chemical-cured bonding to soft or hard tissues, metal, porcelain, ceramic or other surfaces. A potential application for the composition is the holding together, by an overlying layer of resulting polymer, tissues adjacent to incisions and wounds. The polymerized composition might replace suturing, and allow for the healing of soft tissues.

57 Claims, No Drawings

HYDROPHILIC CROSSLINKING MONOMERS AND POLYMERS MADE THEREFROM

This invention was supported in part by USPHS (MERIT) Research grants R37 DE-05129 and P50 DE-09322 to the American Dental Association Health Foundation from the National Institute of Dental Research, Bethesda, Md. The Government has certain rights in this invention.

1. Field of the Invention

Hydrated collagenous assemblages give strength to tendons, ligaments, bones and teeth. Hydrated polysaccharidic assemblages are important in both plant and animal structures. Also, synthetic industrial materials often have hydrophilic and hydrated surfaces. Most of the important structural biological polymers (collagen, cellulose, etc.) and many structural industrial substrates (oxidized or anodized metal alloys, hardened cement aggregates, etc.) are thus hydrophilic and hydrated when in typical environments.

However, the emphasis in recent research on adhesives for industrial and other applications has been on the development of hydrophobic monomers and polymers. In particular, most prior art dental resins, the derived "vinyl ester resins" used in industry, and most polyester resins, which polymerize by rapid free-radical mechanisms, do not adhere well to moist surfaces, or to hydrophilic substrates exposed to water. The success of dental adhesive composition bonding by current methodologies is limited due, at least in part, to a partitioning of the various components such as initiators, promoters, and monomers as they diffuse into the substrate material. This partitioning or separation effect, resulting from different solubility characteristics of the monomers, initiators, and other components, separates components that must work together for effective polymerization and consequential adhesive bonding.

The need for monomers that polymerize and crosslink very rapidly, indifferent to the presence of water, with substantial water-solubility and surface-activity characteristics, has not been adequately recognized.

2. Description of the Prior Art

U.S. Pat. Nos. 3,066,112 and 3,194,783 describe an insoluble filling material. The filling material includes a clear, colorless, fused silica filler, a keying agent, such as vinyl trichlorosilane which is used to impart hydrophobic properties to the filler, and a binder made up of a polymerizable resin.

U.S. Pat. No. 4,514,527 describes materials and methods for improving the adhesion of composite materials and resins to dentin, enamel and other substrates. The invention includes a three-step method wherein the first step comprises contacting the surface of the dentin with an aqueous solution comprising an acidic salt containing a cation which is capable of changing valence. The second step involves contacting the surface of the dentin with a solution comprising NTG-GMA in a volatile water-miscible solvent solution. Finally, the dentin surface is contacted with a solution of PMDM and/or BTDA-HEMA in the same or different volatile water-miscible solution.

U.S. Pat. Nos. 4,521,550; 4,588,756 and 4,659,751 are related patents which describe materials and methods for improving the adhesion of composite materials and resins to dentin, enamel and other substrates. The patents describe, inter alia, a method for preparing a dentin surface for adhesion of a composite resin comprising contacting the surface of the dentin with an aqueous solution comprising an acidic salt. Next, the surface is contacted with a solvent containing NPG, NTG-GMA, or NPG-GMA. The dentin surface is finally contacted with a solution consisting of addition reaction products of pyromellitic acid dianhydride and 2-hydroxyethyl methacrylate, or the addition reaction product of 3,3',4,4'-benzophenonetetracarboxylic dianhydride and 2-hydroxyethyl methacrylate, or 4-methacryloxyethyltrimellitic anhydride.

SUMMARY OF THE INVENTION

Affinity and adhesive bonding frequently are associated with materials having similar physiochemical characteristics. Therefore, synthetic monomers, and their formulations that will have physiochemical characteristics similar to hydrated natural and artificial materials would be highly useful as adhesion promoters. Such synthetic monomers could infiltrate these materials on a molecular scale or manifest sufficient affinity for durable bonding to permeable hydrophilic surfaces.

In certain dental or medical applications, it is particularly important to match a monomer and its formulation with the physical characteristics of hydrated collagen such as slightly decalcified dentin or bone surfaces. Collagen, in either its natural or denatured state, may be penetrated, infiltrated, and impregnated by entropic migration of these monomers into the hydrated and/or expanded fibrils or polypeptide chains. These permeated monomer chains become part of the same collagen fibrils that are embedded within the hydroxyapatite of the underlying, unaltered tooth or bone. A strong and lasting bond can be obtained by the thorough polymerization of these monomers in situ. An essential feature of the present invention is the disclosure of novel crosslinking monomers and polymerization initiators, which, utilized together, will equally penetrate such hydrous or hydrophilic substrates, form strong crosslinked polymers, and copolymerize with less-hydrophilic structural resins applied thereupon.

It is therefore useful if the disparate classes of compounds or compositions used in the dental adhesive composition have uniform physical properties. The entire composition, made up of various components, constitutes a major aspect of the invention, in addition to the novelty of individual chemical compositions of matter.

This invention relates primarily to hydrophilic polymerizable adhesive compositions comprising hydrophilic polymerizable monomers; polymerization initiators, accelerators and stabilizers, which may be an integral part of the hydrophilic polymerizable monomer molecules (herein termed "hybrid hydrophilic monomers"), or separate therefrom; a dianhydride component, which when reacted with the hydrophilic monomers in the presence of a catalyst (optionally the same as the amine polymerization accelerator) gives rise to a polyfunctional monomer intermediate; and, preferably, water.

The preferred hydrophilic polymerizable monomers are dimethacrylates and/or diacrylates containing one or more (preferably two) carboxyl groups, with connective moieties that, together with the carboxyl groups, provide sufficient affinity with water to allow any desired amount of water and/or miscible fugitive solvents to be mixed homogeneously with these monomers and formulations containing them. The activity of water can thereby be made equal to that in biological tissues, which will promote biocompatibility and enhanced adhesive characteristics of polymers prepared from these formulations. The quintessential monomers have one or more carboxyl groups per monomeric molecule, preferably two or three carboxyl groups, one or more methacrylate or acrylate groups, preferably two or more methacrylate groups, and controllably hydrophilic segments within the monomer molecules serving as connectors between the polymerizable groups and the carboxyl groups.

This invention teaches statistical formulas and means to prepare useful mixtures of hydrophilic polymerizable monomers containing hybrid hydrophilic polymerizable monomers having desirable degrees of hydrophilicity and adhesive characteristics for moist and/or hydrophilic substrate surfaces. The formulas make it possible to calculate the molar proportions of reactive reagents, "RR", (for example, HM/HA, a molecule containing at least one polymerizable moiety and also containing one reactive hydroxyl group or primary, or secondary amino group; "PC", a reagent molecule containing one reactive hydroxyl group or primary, or secondary amino group together with a polymerization co-photoinitiator functionality; "PA", a reagent molecule containing one reactive hydroxyl group or primary, or secondary amino group together with a polymerization accelerator; "PS", a reagent molecule containing one reactive hydroxyl group or primary, or secondary amino group together with a polymerization stabilizer functionality; "W", a water molecule; and/or F, another functional moiety); relative to the molar proportions of dianhydrides to obtain monomeric mixtures with the desired proportions of various reactive groups on molecules of the monomer composition.

The formulas are: If K=the number of moles of a given kind of RR per mole of dianhydride "D", and p=the probability of one of the reactive groups, such as an anhydride group, on D that has not reacted; then the component proportionalities are: p [unsubstituted D moles]=$(K/2)^2$ or $K=2(1-p^{\frac{1}{2}})$. K can be selected at any desired level. The most preferred adhesive monomer formulations contain, on a relative basis, reaction products of one mole of a dianhydride with 1.55 to 1.99 moles of a HM/HA compound. Thus, probability statistics are disclosed that optimize compositions of reaction products. Additionally, an equation is given to greatly simplify the determination of the proportions of eutectic mixtures of high-melting reagents and/or reaction products to make possible newer and more economical means to synthesize and utilize the new formulations.

These hydrophilic monomers are formed and/or formulated with compounds that are equally hydrophilic and surface-active and which stabilize the monomers and initiate polymerization of the monomers from surface-bound and intrasubstrate locations. Thus, also disclosed herein are novel, dual-purpose synthesis reaction catalysts, stabilizers, and polymerization initiators that have solubility and surface-activity characteristics like those of the monomers so that they will not be separated by partitioning during penetration of the monomers into the substrate adherends, an important feature of the invention. In one embodiment, the hydrophilic monomer itself contains as a substitutent the polymerization accelerator, preferably an amine.

Thus, the present invention includes, inter alia, novel crosslinking monomers and polymerization initiators, that, when utilized together, will each equally penetrate hydrous or hydrophilic substrates to form a strong crosslinked polymer, and that will copolymerize with structural resins having a low hydrophilicity.

The hydrophilic adhesive monomer composition may include water, a miscible fugitive solvent, or a combination thereof. In the present system, an optimal amount of water, with or without fugitive solvents (that is, miscible solvents that are volatile and/or rapidly or readily diffuse out of the materials of interest, e.g., acetone, alcohol, and the like) is preferably incorporated as an integral part of the polymer during its polymerization. Also, water can be imbibed, sorbed, or otherwise incorporated from hydrous environments during diffusion of these synthetic molecules into the substrate material and/or after polymerization occurs in situ. The high crosslink density of these polymers containing water gives greater strength, durability, and dimensional stability. At least one viscosity-controlling, water miscible monomer may also be present.

The monomers can thereby be formulated not only to be isotonic with respect to physiological saline solutions and body fluids, if desired, but also are uniquely polyfunctional leading to highly crosslinked polymers capable of a continuously variable water content, yet having unusual strength, stiffness, and stability.

More specifically, monomer formulations have been conceived that can incorporate any desired optimum concentration of water and/or miscible, fugitive solvents into the monomeric formulation making it compatible with soft and hard biological tissues, and with hydrophilic, hydrated and/or moist surfaces in industrial adhesive applications. Even though or when these formulations contain water, they can polymerize rapidly to form strong polymers having unique characteristics.

A surprising advantage of the crosslinking polymeric systems, containing an optimal water content at the time of polymerization, with monomer formulations such as those described herein, is the increased dimensional stability due to decreased water absorption of the polymeric product when it is subjected to moisture, and the existence of $H_2O$ diffusion paths for volumetric relaxation of localized stresses during polymerization, adhesive bonding, and hardening. Otherwise, stress concentrations limit adhesive bond strengths and other desirable properties.

A problem solved by the monomer composition of this invention is the need for a fluid adhesive that does not require organic solvents, yet which hardens in seconds in the presence of water due to the influence of hydrophilic polymerization initiators. A related feature of the present invention is the preparation and formulation of all the necessary polymerization ingredients so that they will have substantially identical solubility characteristics, especially with respect to hydrophilicity and surface-activity, as mediated by carboxyl and other groups, so that their diffusion coefficients into substrate tissues such as hydrated collagen will coincide, and the components will be present together in approximately the same amount at all depths of substrate penetration. This characteristic of each ingredient is essential for optimum polymerization, copolymerization, and consequential adhesive bonding and durability of the resulting "monolithic" structure.

Bonding of the equally penetrated composition components is achieved by interdiffusion, interpenetration and polymerization of the monomers within the tissues. An important feature of the present invention is that the synthetic polymeric material forms a "concentration gradient" at the interfacial region, forming a continuum of structurally sound substrate. The concentration of the substrate gradually decreases, and the concentration of the artificial polymer increases out to the neat or reinforced structural resin, as the distance from the substrate increases.

Such a "concentration gradient" can be achieved only by matching the physical and chemical characteristics, including the water contents, of both the substrate and the monomer formulation. The ionizable carboxyl groups of the monomers should have an acidifying effect. The acidifying effect tends to make the substrate more cationic by protonating amino and carboxylate groups. This will cause the substrate soft tissues to expand by virtue of charge repulsion. If the substrate is already denatured, the ionic effect will tend to expand basic or amphoteric material and promote interpenetration by ionic and/or entropydriven diffusion of the monomers into accessible interchain spaces occupied by water. Also, these monomers become anionic after proton dissociation and therefore interactive and attracted to the positively charged substrate.

A significant aspect of this invention is therefore the combined utilization of the various components of the polymerizable composition of this invention. Although the compounds and compositions shown in the different formulations represent different kinds of molecular structures, it is important that they be considered and used together.

This invention further contemplates a kit containing the components thereof. For example, such a kit may include a polyfunctional monomer intermediate composition or precursors thereof. The kit may comprise a container holding a polyfunctional monomer intermediate produced by the reaction of a dianhydride with a compound containing at least one free hydroxyl group, one primary or secondary amine group or a combination thereof, and at least one polymerizable vinyl group, the reaction catalyzed by an amine; a polymerization inhibitor suitable for use during synthesis and storage of the monomer; water, a miscible fugitive solvent, or a combination thereof; and a hydrophilic, surface-active polymerization initiator.

This invention also contemplates a method for applying the inventive hydrophilic adhesive compositions to a substrate, and includes the polymers resulting from polymerization of the inventive compositions.

The novel combination of properties of these hydrophilic adhesive monomers and their formulations provides for an unprecedented variety of potential uses in dental, medical and industrial applications where adhesiveness is of value, especially where adhesive bonding is desired to hydrophilic and/or wet substrates. For example, it is conceivable that some of these formulations might be used for chemical- or light-cured bonding to soft tissues for applications such as the holding together, by an overlying layer of resulting polymer, the tissues adjacent to incisions and wounds (to replace suturing) until healing occurs.

DESCRIPTION OF PREFERRED EMBODIMENTS

This invention includes a composition of matter comprising novel monomers, polymerization initiators, and polymers compatible with water and hydrous environments.

It also includes a method of using the composition, and a kit including the composition. The monomers can be formulated to be isotonic with respect to physiological saline solutions and body fluids. The monomers are also uniquely polyfunctional leading to highly cross-linked polymers capable of a continuously variable water content, yet having unusual strength, stiffness, and stability.

The hydrophilic monomer compositions of the present invention preferably comprise reaction products of preferably dianhydrides with reactive reagents, "RR", which include "HM/HA". A HM/HA is defined as a polymerizable molecule preferably containing at least one or more methacrylate and/or acrylate groups connected to at least one free hydroxyl group or primary or secondary amino group; the connecting moieties may be comprised of one or more —$CH_2$— groups, —$CH_2CH_2O$— groups, —$CH(CH_3)CH_2O$— groups, —$CH(CH_3)CH_2$— groups; or cyclic aliphatic, heterocyclic aliphatic, or aromatic components; or combinations of these components. Preferred HM/HA's containing more than one methacrylate or acrylate group connected to at least one free hydroxyl group are exemplified by glycerol dimethacrylate and glycerol diacrylate. The connecting moiety should not contain functionalities that prevent polymerization of the resulting monomers. Examples of other RR are given below.

The hydrophilic moieties within the monomer molecules include the carboxyl groups and the connecting segments between polymerizable and carboxyl-containing moieties. The connecting segments provide optimal lengths for crosslinking efficiency of the polymerizable, preferably methacrylate, groups by providing an adequate sphere of access of one unreacted polymerizable group to free radical sites of neighboring chains undergoing polymerization. This is important because the reactive site on the growing polymeric chain in viscous resins (monomer formulations, in this case) is localized in space because of the size and configuration of the polymeric chain. The optimally considerable lengths affect the physical properties of the monomer, and resulting polymer produced from the monomer. The optimally considerable length can be varied depending upon the application. An optimally considerable length lies between a short length that results in an inflexible, sometimes brittle polymer with lower hydrophilicity, and a long length that results in a soft polymer with poor strength properties. Generally with dentin bonding, a length that produces a monomer having hydrophilic properties similar to the dentin substrate is desired.

The term "carboxyl groups" used with respect to the monomers or other components of the invention can include protonated carboxyl groups, dissociated carboxylate groups, salts, amine complexes, esters, amides, and/or other derivatives.

The nature of these formulations is such that fluoride-releasing compounds can be incorporated, and the water content of the monomers and/or their polymers can provide a slow release of fluoride ions as desired, for example in dental restorative or caries-preventive materials.

The hydrophilic adhesive monomer compositions of this invention include polyfunctional monomers and intermediates that are produced by the reaction of reactive reagents, RR (which include HM/H compounds), with dianhydrides. The reactions of the dianhydrides with the HM/HA and other RR compounds are carried out by heating and/or catalyzed with tertiary amine catalysts or other catalysts known to the art.

The polyfunctional monomers and intermediates of the invention are preferably liquids comprising the reaction products of one or more dianhydride components with HM/HA and other RR, and the reactions can be catalyzed by an amine polymerization cophotoinitiator or polymerization accelerator wherein the amine moiety is an integral part of some of the polymerizable surface-active molecules of the reaction products. Likewise, and in combination, the hydrophilic monomers can have at least one polymerization inhibitor moiety as an integral part of some of the polymerizable surface-active molecules.

Eutectic mixtures of high-melting and relatively insoluble dianhydrides or monomers find beneficial use in the synthesis and compositions. The eutectic mixtures are approximated by the formula: $X = 100(T_2 - T_e)/T_1 + T_2 - 2T_e$, where X is the mole percentage of lower-melting dianhydride or monomer component, $T_1$ is the melting point of the lower-melting dianhydride or monomer component, $T_2$ is the melting point of the higher-melting dianhydride monomer or component, and $T_e$ is the eutectic temperature, the temperature at which the first sign of melting of the mixture occurs. This formula is useful to facilitate the determinations of eutectic compositions of high-melting dianhydrides for utilization in some cases to avoid the necessity of using elevated temperatures that might induce premature polymerization during the synthesis of the monomer mixtures. It is also useful to use this relationship to provide monomer formulations in the preferred liquid form, which might otherwise form crystalline solids. It is preferred that the eutectic temperature for the resulting monomer formulations be less than about 25° C., or room temperature.

The molar composition of a ternary eutectic mixture can be determined more readily by using the corresponding binary equilibrium diagrams. The three binary diagrams are incorporated as sides of an equilateral triangular ternary diagram, bisecting the internal angles of an internal triangle formed by connecting with the theoretical binary eutectic composition points, and using the intersection of the bisecting lines as a hypothetical approximation of the ternary eutectic composition. Use of such diagrams facilitates the synthesis of neat liquid adhesive monomer formulations free of solids without the use of solvents that would otherwise add to the cost, inconvenience, and other problems associated with large-scale production and applications.

The composition includes one or more amines preferably selected from the group comprising hexamethylenetetramine (methenamine), 1,4-diazabicyclo[2.2.2]octane (DABCO), quinuclidine, N,N-dimethylethanolamine (2-dimethylaminoethanol), N,N-diethylethanolamine, N-ethyldiethanolamine (2,2'-ethyliminodiethanol), triethanolamine, N,N-dihydroxyethyl-p-toluidine, 3-quinuclidinol, N,N-dihydroxyethylglycine, N-(2-hydroxyethyl)iminodiacetic acid, N-hydroxyethylethylenediaminetriacetic acid, N,N-dimethylglycine, 2-quinuclidine carboxylic acid, the reaction product of 2,3-quinuclidinol with a dianhydride, N,N-dimethylaminoethylmethacrylate, the reaction product of 3-quinuclidinol with an organic anhydride, N,N-diethylaminoethylmethacrylate, and 2,6-di-tert-butyl-4-(dimethylamino)methylphenol.

The hydrophilic adhesive monomer composition also includes a polymerization initiator and a polymerization inhibitor, and may optionally contain water, a water-miscible solvent, one or more reactive diluents, and/or an inert solvent.

The polymerization initiators are preferably selected from the group comprised of camphorquinone-10-sulfonic acid and its salts, anti-(1R)-(+)-camphorquinone 3-oxime, anti-(1S)-(−)-camphorquinone 3-oxime, the addition reaction product of anti-(1R)-(+)-camphorquinone 3-oxime or anti-(1S)-(−)-camphorquinone 3-oxime with an organic anhydride or a dianhydride, camphorquinone and peroxides.

Free-radical chain-forming polymerization requires the movement of the unsaturated vinyl groups to the spatially fixed sites of radical atoms to which they become attached. Therefore, it is most advantageous to have surface-bound polymerization initiators that allow mobile monomer molecules to approach, add on to their free-radical sites, and polymerize away from the substrate surface.

The polymerization inhibitors or stabilizers are preferably selected from the group comprised of the reaction product of 4-hydroxymethyl-2,6-di-tert-butylphenol with a dianhydride, 2,5-ditertiary butyl hydroquinone, monotertiary butyl hydroquinone, 3,5-di-t-butyl-4-hydroxy-hydrocinnamate, 4-hydroxy-3,5-di-tert-butylphenyl propionic acid, 3,3'-thiodipropionic acid, 3,5-di-t-butyl-4-hydroxyanisole, p-benzoquinone, the monomethyl ether of hydroquinone, hydroquinone, and 2,6-di-tert-butyl-4-(dimethylamino)methylphenol, and, most preferably 4-hydroxymethyl-2,6-di-tert-butylphenol, also known as 3,5-di-tert-butyl-4-hydroxybenzyl alcohol (Frinton Labs., Vineland, N.J.).

The viscosity-controlling monomers are preferably selected from the group comprised of Polyethylene Glycol 400 Dimethacrylate; Polyethylene Glycol 600 Dimethacrylate; Polyethylene Glycol 400 Diacrylate; PEG 1,000 Dimethacrylate; polypropylene glycol dimethacrylate; triethylene glycol di(meth)acrylate; and water-miscible, low-viscosity liquid dimethacrylates, diacrylates, monomethacrylates, and monoacrylates.

The present invention provides a means by which a broad spectrum of novel surface-active, adhesive, cross-linking monomers, which polymerize by a free radical mechanism, can be produced by novel synthesis methods. The monomer synthesis catalysts can be incorporated as moieties of the surface-active hydrophilic monomer molecules, and/or retained in the monomer synthesis reaction products as separate discrete molecules, or removed from the reaction products. The retained monomer synthesis catalyst can function, at a later time, to bring about the polymerization of these monomers yielding polymers with improved adhesion qualities and other desirable characteristics not before available.

This invention contemplates (incorporates) the use of formulas to determine the useful mixtures of hydrophilic polymerizable monomers, hybrid hydrophilic polymerizable monomers, polyfunctional monomer intermediates, catalysts, stabilizers, and polymerization initiators, each formulation having unique and desirable degree of hydrophilicity and adhesive characteristics for moist and/or hydrophilic substrate surfaces. The formulas are used to calculate the molar proportions of one or more "reactive reagents," "RR", (for example, HM/HA, a molecule containing at least one polymerizable moiety, preferably at least one methacrylate and-/or one acrylate group, most preferably two or more methacrylate groups, and also containing one reactive hydroxyl group or primary, or secondary amino group; PC, a reagent molecule containing one reactive hydroxyl group or primary, or secondary amino group together with a polymerization cophotoinitiator functionality such as a tertiary amino group; PA, a reagent molecule containing one reactive hydroxyl group or primary, or secondary amino group together with a polymerization accelerator such as tertiary aromatic amino group; PS, a reagent molecule containing one reactive hydroxyl group or primary, or secondary amino group together with a polymerization inhibiting stabilizer functionality such as an aromatic, preferably sterically hindered, hydroxyl group; W, a water molecule, to form "extra" carboxyl groups from residual anhydride groups; and/or F, another functional moiety, examples of "F" reagent molecules being diols, diamines, UV-absorbing moieties, reactive impurities, etc.), relative to the molar proportions of a "difunctional" reagent "D" (for example, a molecule containing two essentially or approximately equally and independently reactive anhydride groups) to obtain monomeric mixtures with the desired proportions of various reactive groups on molecules of the monomer compositions. This option to react the reaction sites on D molecules with different kinds of reagents (RR) in any desired concentration or proportion can provide novel formulations with especially valuable characteristics.

The formulas to determine the desired useful mixtures of components are as follows: K=the number of moles of a given kind of RR per mole of D, and p=the probability of one of the reactive groups, such as an anhydride group, on D that has not reacted; then the component proportionalities in the formulation can be determined from the following formulas: p [disubstituted D moles]=$(K/2)^2$; p [monosubstituted D moles]=$K(1-K/2)$; and p [unsubstituted D moles]=$(1-K/2)^2$ or $K=2(1-p^{\frac{1}{2}})$. K can be selected at any desired or acceptable level from about 0 up to about 2.0, preferably from about 1.55 to about 1.99, for the first reagent RR, typically a HM/HA, and one or more other kinds of reagents RR used to react with the balance of the functional groups of D. (Of course, appropriate adjustments can be made when the reactive groups are not equally and independently reactive.)

When trianhydrides are used, analogous probability statistical relationships are used.

The most preferred adhesive monomer formulations contain, on a relative basis, reaction products of one mole of a dianhydride with 1.55 to 1.99 moles of an HM/HA compound, plus PC, PA, PS, W, and/or F so that the sum of the moles of HM/HA plus PC, PA, PS, W, and F is between about 1.55 and at least 2. The reaction to produce these monomers can be catalyzed by the incorporation of a PC and/or a PA, with PS present to prevent premature polymerization. 4-(Dimethylamino)phenethyl alcohol is a PC and/or PA utilized in Example 2. The most preferred adhesive monomer formulations are comprised of reaction products of one mole of a dianhydride with 1.55 to 1.99 moles of an HM/HA compound together with no more than about 0.45 to 0.01 moles of a PS, W and/or F (which formulation thereby contains desired concentrations of hybrid hydrophilic monomers). PC and/or PA molecules can be added to formulations in which the anhydride groups have already been completely reacted, but preferably they are reacted with anhydride groups to gain surface-binding carboxyl groups on the same molecule. Surface-active accelerators and/or cophotoinitiators of polymerization are valuable for initiating polymerization from surface-bound molecules. Such a compound is described in Example 2.

Preferably, one of the other reagents RR comprises a molecule containing a tertiary amino group and a hydroxyl group or a primary or secondary amino group. For example, in the presence of trace amounts of a polymerization inhibitor or stabilizer, 2-dimethylaminoethanol or 4-(dimethylamino)phenethyl alcohol can catalyze the polyfunctional monomer intermediate synthesis, become attached to some of the monomeric molecules, serve as a polymerization accelerator and/or cophotoinitiator, and possibly improve bonding to surfaces of certain glass, metallic, and other surfaces by complex formation. These surfaces include those of dental materials such as porcelains, ceramics, amalgams, gold, cast alloys, and teeth.

The novel hydrophilic monomers and polymerization initiators of this invention are surface-active in nature; that is, the hydrophilic monomers penetrate and infiltrate into or adsorb or chemisorb onto dental or other substrates. The absorbed or chemisorbed hydrophilic monomers and polymerization initiators form a concentration gradient on the surface of, or within, the substrate and react with one another to produce free radical polymerization initiation sites upon and within the substrate. The free radical sites can then be added onto by double-bonded carbon vinyl groups, or other groups capable of addition and chain-forming polymerization. The carbon vinyl group-containing compounds grow outward from initiation sites on the substrate site into the bulk of overlying monomers, forming crosslinked polymers that are intimately, multiply, and densely bonded to the substrate surface.

Currently available coupling agents that have surface binding groups and a polymerizable vinyl group attached to the same molecule are not optimal in their ability to produce dense populations of covalent linkages between polymers and substrate surface attachment sites. It is only by infrequent chance that a growing polymer chain, the reactive site of which is fixed or localized in space at any given instant, has freely mobile monomer groups add to it so as to fortuitously lead growth to the location of a copolymerizable vinyl group attached to the substrate surface. The hemisphere of mobility and access of the methacrylate, acrylate, or other vinyl group of a surface-bound coupling agent is limited. A vinyl group is added to a growing polymer chain only when the radical site is brought, by chance, by the addition of other mobile monomers, within this hemisphere of its mobility. Further addition of monomers or neighboring vinyl groups from there is limited due to restrictions imposed by steric hindrance factors.

A detailed description of each of the components which comprise the hydrophilic adhesive monomer composition of this invention is found immediately below.

HYDROPHILIC MONOMERS AND MONOMER INTERMEDIATES

The monomer formulations of this invention produce polymers with a high crosslink density. The high crosslink density of the water-containing polymers gives greater strength, durability, and dimensional stability to the polymer. In the present system, an optimal amount of water, with or without fugitive solvents becomes an integral part of the polymer during its polymerization. Fugitive solvents are miscible solvents, e.g., acetone, alcohol, etc., including water, that are volatile and/or rapidly or readily diffuse out of the materials of interest. Water can also be imbibed, sorbed, or otherwise incorporated from hydrous environments into the formulation during diffusion of the composition into and onto the substrate material before or after polymerization occurs.

Polymers prepared from these crosslinking, controllably-hydrophilic monomers have improved dimensional and adhesive characteristics during and after polymerization when they contain an optimum content of water or other appropriate solvent during polymerization. The improved dimensional and adhesive characteristics are due to three properties of the polymer. First, the three-dimensional polymeric networks have a "structure memory" characteristic. Second, the degree of polymerization, which is indirectly related to the percentage conversion of polymerizable groups to polymeric segments, and the degree of crosslinking, is limited under ambient conditions by the increasing viscosity that accompanies the rise of $T_g$ (the glass transition temperature) of the polymerizing resin relative to the temperature at which polymerization is taking place. Finally, the resulting polymer has a quasi-equilibrium water content which is dependent on the concentration and kinds of hydrophilic groups within the structures.

The water quasi-equilibrium of the polymers derived from the monomers and formulations described, depends on environmental pH, osmolality, temperature, pressure, and other factors. The variability of the innate hydrophilicity of the monomers and other components, as provided for in the present invention, is therefore of great importance for success in specific applications.

Hydrophilic monomers and formulations employing hydrophilic monomers described below are soluble in water in an amount ranging from about 1% by weight to about infinite, or 100% miscibility. The hydrophilic monomers are capable of dissolving at least 1% by weight of water in the monomeric formulations. The proportion of carboxyl groups, connecting segments, and other components of the monomer determines the hydrophilicity of the formulation.

An important feature is the liquid nature of the monomers, which distinguishes them from some previously disclosed monomers that form crystalline monomeric solids. There is an advantage in the liquid nature of these new monomers, as distinguished from PMDM (the reaction product of two moles of HEMA, hydroxyethylmethacrylate, with one mole of PMDA, pyromellitic dianhydride), which forms a monomeric crystalline solid. The new monomers and formulations containing them do not need to be dissolved in solvents or other liquids before application. The viscosities of the monomer formulations can be adjusted to optimum levels by the use of water, water-miscible solvents, and/or monomers of low viscosity such as water-soluble methacrylates or acrylates, preferably dimethacrylates or diacrylates, that are incorporated into the composition prior to polymerization.

The preferred liquid monomers will have one or more carboxyl groups per molecule, preferably two carboxyl groups; one or more methacrylate or acrylate groups per molecule, preferably two methacrylate groups; and segments within the monomer molecules that can be controlled with regard to the degree of their hydrophilicity and that serve as connectors between the polymerizable groups and the carboxyl groups.

The carboxyl groups in the monomers, or in other ingredients in the monomer composition, can be present in the form of protonated carboxyl groups, dissociated carboxylate groups, salts, amine complexes, esters, amides, and/or other derivatives.

Single-, two-, or multi-component systems can be formulated and used to bring about polymerization of the desired monomers based upon their ultimate end use. Such monomer compositions may be comprised of molecules containing methacrylate, acrylate, vinyl, or other groups capable of free-radical polymerization; one or more amines, the amines preferably selected from the group comprising hexamethylenetetramine (methenamine), 1,4-diazabicyclo[2.2.2]octane (DABCO), quinuclidine, N,N-diethylethanolamine (2-diethylaminoethanol), N-ethyldiethanolamine (2,2'-ethylaminodiethanol), triethanolamine, N,N-dihydroxy-p-toluidine, 3-quinuclidinol, N,N-dihydroxyethylglycine, N-(2-hydroxyethyl)iminodiacetic acid, and N-hydroxyethylethylenediaminetriacetic acid, N,N-dimethylglycine, 2-quinuclidine carboxylic acid, the reaction product of 3-quinuclidinol with one or more dianhydrides selected from Formulations 1, 3, 5, 7, 8, 9, 11, 12, 13, 16, 17, and 18 below, N,N-dimethylaminoethylmethacrylate, N,N-diethylaminoethylmethacrylate, the reaction product of 3-quinuclidinol with an organic anhydride, such as succinic anhydride, maleic anhydride, glutaric anhydride, phthalic anhydride, etc., and tertiary aromatic amines; and one or more polymerization initiators selected from the group consisting of camphorquinone-10-sulfonic acid, camphorquinone 3-oximes, the addition reaction products of camphorquinone 3-oximes with an organic anhydride (such as succinic anhydride, maleic anhydride, glutaric anhydride, phthalic anhydride, etc.) or a dianhydride such as those exemplified in Formulations 1, 3, 5, 7, 8, 9, 11, 12, 13, 15, 17, and 18, camphorquinone, and peroxides, such as benzoyl peroxide, hydrogen peroxide, t-butyl hydroperoxide, etc., and lithium, sodium, or potassium para-toluene sulfinate.

AMINE CATALYSTS

Hexamethylenetetramine, 1,4-diazabicyclo[2.2.2]octane, quinuclidine, and tertiary aliphatic and ring-substituted aromatic amines possessing one or more, preferably multiple, hydrogen atoms on carbon atoms adjacent to the tertiary amino nitrogen atoms are particularly effective for catalyzing the reactions between the hydroxyl groups of the methacrylate or acrylate reagents and the anhydride groups of the dianhydride reagents, and can then be retained in the resulting hydrophilic monomer formulations where they can serve as cophotoinitiators with camphorquinone and other photoinitiators. As cophotoinitiators, the amines, together with photoinitiators, initiate monomer polymerization when activated by a visible light source. Other catalysts, including tertiary amines such as triphenylamine, N,N-dimethylaniline, pyridine, and tribenzylamine can be used, but are less preferred.

Amines such as N,N-diethylethanolamine, N, N-dimethylethanolamine, N-ethyldiethanolamine, triethanolamine, N,N-dihydroxy-p-toluidine, 3-quinuclidinol, 4-(dimethylamino)phenethyl alcohol, and other tertiary amines having hydroxyl groups can provide catalytic activity during synthesis of the monomers and for the synthesis of polymers during the subsequent co-photoinitiating step, allowance being made for the stoichiometry of anhydride groups and total hydroxyl groups. This is so because, with hydroxyl-containing amine catalysts, the amine moieties become attached and integral to some of the monomeric molecules. Similar stoichiometric considerations apply when amino acids such as N,N-dihydroxyethylglycine, N-(2-hydroxyethyl)iminodiacetic acid, and N-hydroxyethylethylenediaminetriacetic acid are used as catalysts.

Other catalysts useful in hydrophilic monomer production are amino acid catalysts that do not form addition reaction products with the monomers. Such amino acids include N,N-dimethylglycine and 2-quinuclidine carboxylic acid. For example, a reaction product of 2 moles of 3-quinuclidinol per mole of a dianhydride, as described in Formulations 1, 3, 5, 7, 8, 9, 11, 13, 15, 17, and 18 below, would not form addition reaction products with the anhydrides during the syntheses, but acid with an ethylene oxide such as SIPOMER® HEM and HEM ETHOXYLATES, manufactured by Alcolac, Linthicum, Md., according to reaction sequence A below.

In Sequence A for example, one mole of 5-[2,5-Dioxotetrahydro-3-furanyl]-3-cyclohexene-1,2-dicarboxylic anhydride, is reacted with mono- and poly(ethyleneglycol) monomethacrylates, in the presence of at least one tertiary amine or other catalyst, where RR is between 1 and 10 moles, HM/HA is preferably 1.55 to 1.99 moles, n and n' are between 1 and 20, and where there are preferably no more than about 0.45 to 0.01 moles of PS, W, and/or F per mole of the dianhydride.

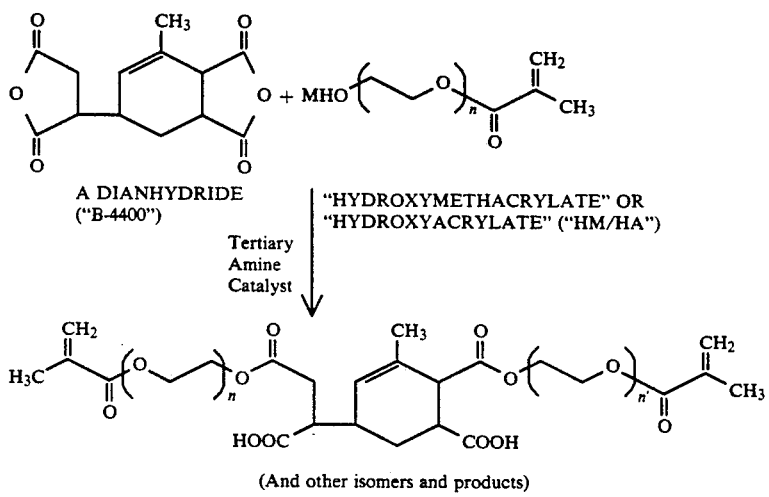

would still be especially valuable as a surface-active cophotoinitiator when the monomers are eventually polymerized.

Other amines that are capable of associating with carboxyl groups of the hydrophilic monomers formed, catalyzing the synthesis of the monomers, and subsequently polymerizing the monomer formulations by cophotoinitiation in conjunction with camphorquinone and/or other photoinitiators are described below. These other amines include N,N-dimethylaminoethylmethacrylate and N,N-diethylaminoethylmethacrylate. These amines are monomers that can copolymerize with the monomers of the present invention.

A particularly interesting tertiary amine which can simultaneously serve as a catalyst for the syntheses of the monomers; prevent premature polymerization, i.e., is useful as an inhibitor/stabilizer; and can later act synergistically with polymerization photoinitiators is 2,6-Di-tert-butyl-4-(dimethylamino)methylphenol.

Tertiary amines that are attached to solid supports or that are in the form of polymers, such as, for example, poly(vinyl pyridine), can be used when it is desired to remove the catalyst from the hydrophylic monomer reaction products by simple filtration methods. This can be valuable in terms of storage stability of the monomers and in giving greater latitude in subsequent formulations.

FORMULATION 1

One formulation of hydrophilic adhesive polyfunctional monomer intermediates is the reaction product of a dianhydride such as "EPICLON B-4400", manufactured by DIC Americas, Inc., Carson, Calif., with an "HM/HA" such as a reaction product of methacrylic

HYDROPHILIC MONOMERS TYPE A RESULTING FROM REACTION SEQUENCE A

When the moles of the hydroxymethacrylate or the hydroxyacrylate produced by reacting methacrylic or acrylic acid and ethylene oxide, as in Formulation 1, range between 1.55 and 1.99 for each mole of the reacted dianhydride, then some molecules of the mixture of monomers will contain a residual anhydride group and one HM/HA group. Most of the other molecules in the mixture of monomers will contain two HM/HA groups. At the lower limit of 1.55 in the preferred range, no more than about 5% of unreacted dianhydride optionally remains in the reaction product, optionally to be reacted with PC, PA, PS, W, and/or F. Above two, the upper limit of the preferred range, in a less-preferred range of between 2 and 4, residual hydroxide groups of HM/HA would remain in the reaction mixture. Residual HM/HA hydroxide groups might be useful in applications which require additional hydrophilicity, or in heat-cured applications to bring about additional crosslinking as a result of condensation reactions between the residual HM/HA hydroxyl groups and the carboxyl groups formed in the initial reaction sequence.

HM/HA compounds are commercially available or readily synthesized. They include HM/HA with polymethylene (oligomethylene) connecting moieties to provide less-hydrophilic monomers. Glycerol dimethacrylate, glycol monomethacrylates, polyethylene glycol monomethacrylates, propylene glycol monomethacrylates and oligopropylene glycol monomethacrylates can be used in the formulations in pure form, or they can first be reacted with anhydride compounds. Polypropylene oxide (oligopropylene oxide) and, especially, polyethylene oxide (oligoethylene oxide), as connecting groups, provide increasingly hydrophilic characteristics to the resulting monomer and polymer formulations.

Optimum spacial separation between methacrylate groups leads to maximum crosslink densities and crosslinking efficiencies. High crosslink density of polymers gives the best strength and durability to water-containing thermoset resins. A high polymer crosslink density and structural and dimensional stability is important, especially when water is incorporated as an integral part of the polymer. In this case, the "plasticizing" water is contained within the monomer formulation during the polymerization, and/or is imbibed, sorbed, or otherwise incorporated from surrounding hydrous environments during and/or after polymerization occurs in situ.

1.55 to 1.99, n is between 1 and 20, preferably between 5 and 6, and where there are preferably no more than about 0.45 to 0.01 moles of PS, W, and/or F per mole of dianhydride. Mixed isomers similar to those shown in reaction sequence A of Formulation 1 are products of the reaction, except that the n and n' segments consist of propylene ether units instead of ethylene ether units. The polymerizable ester groups can be either acrylate or methacrylate, the latter being preferable.

FORMULATION 3

Another formulation of hydrophilic adhesive polyfunctional monomer intermediates is the reaction product of one mole of a dianhydride such as "s-BPDA" (symmetrical-biphenyl tetracarboxylic dianhydride) with preferably 1.55 to less than about 2 moles of a HM/HA such as glycerol dimethacrylate. The monomers are produced according to the following reaction sequence B:

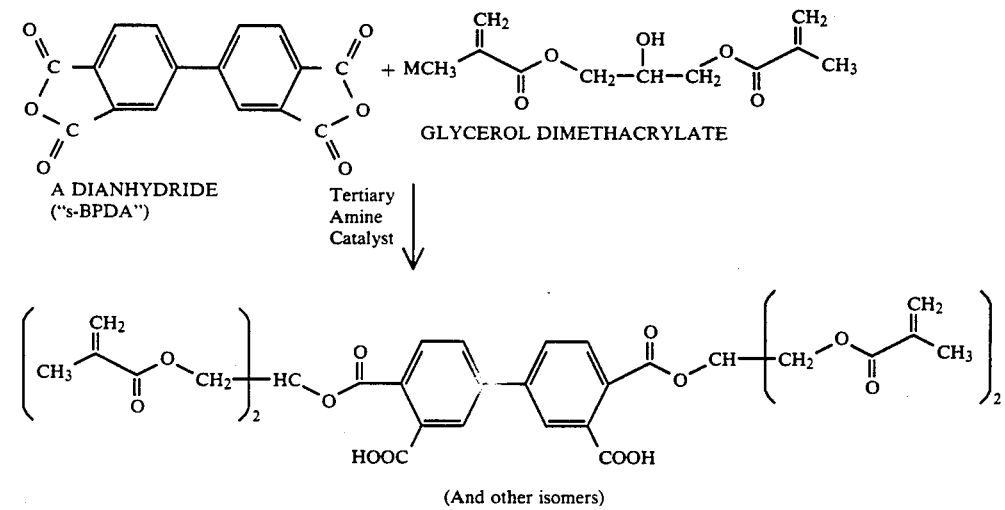

A preferred monomer formulation comprises the reaction products of one mole of a dianhydride with 1.55 to less than about 2.0 moles of a compound containing one free hydroxyl group and at least one polymerizable vinyl group, an optimal content of water, compounds to inhibit polymerization and stabilize the formulation, and polymerization initiators.

FORMULATION 2

Another formulation of hydrophilic adhesive polyfunctional monomer intermediates is the reaction product of one mole of a dianhydride with preferably 1.55 to less than about 2 moles of a HM/HA such as reaction products of methacrylic acid with propylene oxide, these products including polypropylene glycol monomethacrylates, PPGM, symbolized as follows:

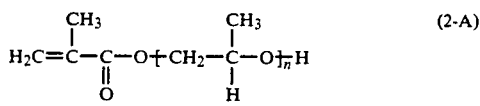

In this example, the dianhydride 5-[2,5-dioxotetrahydro-3-furanyl]-3-cyclohexene-1,2-dicarboxylic anhydride, is reacted with the HM/HA mono- and/or poly-propyleneglycol monomethacrylate in the presence of catalytic amounts of at least one tertiary amine, where RR is between 1 and 4 moles, HM/HA is preferably

HYDROPHILIC MONOMERS TYPE B RESULTING FROM REACTION SEQUENCE B s-BPDA: 3,3',4,4'-biphenyl tetracarboxylic dianhydride, is reacted optionally with heating in a dry volatile aprotic solvent with glycerol dimethacrylate, in the presence of catalytic amounts of at least one tertiary amine, preferably insoluble poly(vinyl pyridine), where RR is between 1 and 10, HM/HA is preferably 1.55 to 1.99, and where there are no more than about 0.45 to 0.01 moles of PS, W, and/or F per mole of the dianhydride.

FORMULATION 4

In this formulation, hydrophilic adhesive polyfunctional monomer intermediates are produced by reacting one mole of a dianhydride such as "s-BPDA", 3,3',4,4'-biphenyl tetracarboxylic dianhydride, with one, or preferably a mixture of more than one, HM/HA reagents such as hydroxy propyl methacrylate, glycerol dimethacrylate, the reaction product of methacrylic acid with propylene oxide such as SIPOMER PPGMM, polypropylene glycol monomethacrylate, symbolized in sequence (2-A) above, and/or other HM/HA reagents wherein the sum of the moles of the various HM/HA is preferably 1.55 to 1.99, the moles of RR are between 1 and 10, and the sum of the moles of PS, W, and/or F are preferably no more than 0.45 to 0.01, per mole of the dianhydride.

The dianhydride, s-BPDA, also referred to as symmetrical-biphenyl tetracarboxylic dianhydride, is reacted with these HM/HA reagents in the presence of catalytic amounts of at least one tertiary amine or other catalyst. The reaction produces mixed isomers and monomeric reaction products with reduced tendency for crystallization of any monomeric species in the hydrophilic monomer formulations. The polymerizable ester groups can be either acrylate or methacrylate, the latter being preferable.

FORMULATION 5

In this formulation, hydrophilic adhesive polyfunctional monomer intermediates are produced by reacting one mole of a dianhydride such as "AC-32", glycerol acetate bistrimellitate [dianhydride], manufactured by Chriskev Co. Inc., Leawood, Kans., with 1 to 10, preferably 1.55 to less than about 2 moles of a HM/HA. AC-32 is also sometimes referred to as polyol trimellitate dianhydride.

FORMULATION 6

In this formulation, hydrophilic adhesive polyfunctional monomer intermediates are produced by reacting eutectic proportions of a dianhydride such as "s-BPDA" and the corresponding proportions of a different dianhydride such as pyromellitic dianhydride (in this case, for example, there would be about 0.42 mole of s-BPDA with about 0.58 mole of pyromellitic dianhydride, according to the previously described formula) with one or more HM/HA reagents such as hydroxyethylmethacrylate in the presence of catalytic amounts of at least one tertiary amine or other catalyst, where RR is between 1 and 10, HM/HA is preferably 1.55 to 1.99 relative to one mole of the mixed dianhydrides, and PS, W, and/or F is preferably less than 0.45 mole. This results in the formation of mixed isomers and monomeric structural types so as to facilitate synthesis, solvent solubility, and penetration and surface interactions with heterogeneous substrates such as dentin, metal alloys, etc. The polymerizable ester groups can be either acrylate or methacrylate, the latter being preferred.

FORMULATION 7

In this formulation, hydrophilic adhesive polyfunctional monomer intermediates are produced by reacting one mole of a dianhydride such as "DSDA", 3,3',4,4'-diphenylsulfone tetracarboxylic dianhydride, manufactured by Chriskev Co. Inc., Leawood, Kans., with preferably 1.55 to 1.99 moles of a HM/HA, produced according to reaction sequences analogous to those illustrated in Formulations 1 and 3. This dianhydride is reacted with the HM/HA in the presence of catalytic amounts of at least one tertiary amine, where RR is between 1 and 10, and PS, W, and/or F is preferably less than 0.45 mole per mole of DSDA.

FORMULATION 8

In this formulation, hydrophilic adhesive polyfunctional monomer intermediates are produced by reacting one mole of 1, 2, 3, 4-cyclopentane dianhydride with preferably 1.55 to 1.99 moles of a HM/HA such as glycerol dimethacrylate in the presence of 0.1 to 0.9 wt % triphenyl phosphine and 0.1 to 0.9 wt % triphenyl antimony and/or other catalysts such as tertiary amines.

The dianhydride is reacted with the HM/HA in the presence of between 1 and 10 moles of RR and preferably no more than 0.45 mole of PS, W, and/or F per mole of dianhydride according to reaction sequences analogous to those illustrated in Formulations 1 and 3. This results in the formation of mixed isomers wherein the polymerizable ester groups can be acrylate or methacrylate, the latter being preferred.

FORMULATION 9

In this formulation, hydrophilic adhesive polyfunctional monomer intermediates are produced by reacting one mole of a dianhydride such as "ODPA," 4,4'-oxydiphthalic anhydride, manufactured by Chriskev Co. Inc., Leawood, Kans., with preferably 1.55 to 1.99 moles of a HM/HA, according to reaction sequences analogous to those illustrated in Formulations 1 and 3. This dianhydride is reacted with a HM/HA in the presence of catalytic amounts of at least one tertiary amine or other catalyst, where RR is between 1 and 10.

FORMULATION 10

In this formulation, hydrophilic adhesive polyfunctional monomer intermediates are produced by reacting one mole of a dianhydride such as ODPA with preferably 1.55 to less than about 2 moles of a HM/HA. The HM/HA is a reaction product of methacrylic acid and a propylene oxide such as SIPOMER PPGMM, polypropylene glycol monomethacrylate, symbolized in 2-A above.

The dianhydride, ODPA, is reacted with the polypropyleneglycol monomethacrylate in the presence of catalytic amounts of at least one tertiary amine, where RR is between 1 and 10, HM/HA is preferably 1.55 to less than about 2, and n is between 1 and 20, preferably between 5 and 6, according to reaction sequences analogous to those illustrated in Formulations 1 and 3. The reaction results in the formation of mixed isomers wherein the n and n' segments (connecting moieties) consist of propylene ether units. The polymerizable ester groups can be acrylate or methacrylate, the latter being preferable.

FORMULATION 11

In this formulation, hydrophilic adhesive polyfunctional monomer intermediates are produced by reacting one mole of a dianhydride such as "6FDA", 4,4'-[Hexafluoroisopropylidene]-bis[phthalic anhydride], manufactured by Chriskev Co. Inc., Leawood Kans., with a HM/HA, according to reaction sequences analogous to those illustrated in Formulations 1 and 3. RR is between 1 and 10, HM/HA is preferably 1.55 to 1.99, and where the sum of the mole of PS, W, and F is no more than 0.45 mole per mole of dianhydride.

FORMULATION 12

In this formulation, hydrophilic adhesive polyfunctional monomer intermediates are produced by reacting mixtures, preferably a ternary eutectic mixture of dianhydrides such as "6FDA", "B-4400", and "s-BPDA" with a HM/HA. The HM/HA can be a reaction product of methacrylic acid and a propylene oxide such as SIPOMER PPGMM, oligopropylene glycol monomethacrylates or polypropylene glycol monomethacrylate, symbolized as 2-A above, other than HM/HA, or a mixture of different kinds of HM/HA.

The mixed dianhydrides are reacted with the HM/HA in the presence of catalytic amounts of at least one tertiary amine or other catalyst, where RR is between 1 and 10, HM/HA preferably 1.55 to 1.99, and the sum of PS, W, and/or F in moles is preferably less than about 0.45 per mole of total dianhydrides, according to reaction sequences analogous to those illustrated in Formulations 1 and 3. This results in the formation of mixed isomers and monomer types to give liquid adhesive resins with affinity for substrates having chemically heterogeneous characteristics. The polymerizable ester groups can be acrylate or methacrylate, the latter being preferable.

FORMULATION 13

In this formulation, hydrophilic adhesive polyfunctional monomer intermediates are produced by reacting mixtures, preferably a binary eutectic mixture (m.p. about 161° C.) of about 0.09 mole, "PMDA," pyromellitic dianhydride, with about 0.91 mole of "B-4400," Chriskev Co. Inc., Leawood, Kans. with one or more HM/HA. A preferred HM/HA is glycerol dimethacrylate reacted according to sequences analogous to those illustrated in Formulation 3, in which the dianhydrides are reacted preferably with heating in air in the presence of catalytic amounts of triphenyl phosphine, triphenyl antimony and/or at least one tertiary amine, where RR is between 1 and 10, HM/HA is preferably 1.55 to 1.99, and where PS, W, and/or F in moles is preferably no greater than about 0.45 moles per mole of total dianhydrides.

FORMULATION 14

In this formulation, hydrophilic adhesive polyfunctional monomer intermediates are produced by reacting one mole of a dianhydride such as PMDA with a HM/HA such as glycerol dimethacrylate, GDM. The dianhydride, PMDA, is reacted with GDM preferably in the presence of a catalyst, for example, at least one tertiary amine, where RR is between 1 and 10, and HM/HA is preferably 1.55 to 1.99, according to reaction sequences analogous to those illustrated in Formulation 3. This results in the formation of mixed isomers containing 2 or more methacrylate groups to produce crosslinking during subsequent polymerization, and 2 or more carboxyl groups for increased reactivity with hydrophilic substrates.

FORMULATION 15

In this formulation, hydrophilic adhesive polyfunctional monomer intermediates are produced by reacting 0.7 mole of "BTDA" 3,3',4,4'-benzophenone tetracarboxylic dianhydride, manufactured by Chriskev Co. Inc., Leawood, Kans., mixed with 0.19 mole of PMDA plus 0.11 mole of s-BPDA, with preferably 1.55 to 1.999 moles of HM/HA, in this case glycerol dimethacrylate in which is dissolved 0.001 mole of 3,5-di-tert-butyl-4-hydroxybenzyl alcohol (a stabilizer, PS, which becomes chemically united with a small proportion of the monomeric molecules).

The monomer is produced according to a reaction sequence analogous to that illustrated in Formulation 3 in which the dianhydride is reacted with the HM/HA and PS in the presence of catalytic amounts of at least one tertiary amine. More generally, RR can be between 1 and 20, HM/HA preferably 1.55 to 1.999, and PS, W, and F in molar quantities suitable for the end-use conditions.

FORMULATION 16

In this formulation, hydrophilic adhesive polyfunctional monomer intermediates are produced by reacting one mole of BTDA with preferably 1.55 to less than about 2 moles of a reaction product of methacrylic acid and a propylene oxide such as SIPOMER PPGMM, polypropylene glycol monomethacrylate, symbolized in FIG. 2-A above.

The dianhydride, BTDA, is reacted with the polypropyleneglycol monomethacrylate preferably in the presence of a catalyst such as at least one tertiary amine. The moles of PPGM are between 1 and 10, preferably 1.55 to 1.99, and n is between 2 and 20, preferably between 5 and 6, both according to reaction sequences analogous to those illustrated in Formulations 1 and 2. The reaction results in the formation of mixed isomers wherein the n and n' segments, connecting moieties, consist of propylene ether units. The polymerizable ester groups can be either acrylate or methacrylate, the latter being preferable.

FORMULATION 17

In this formulation, hydrophilic adhesive polyfunctional monomer intermediates are produced by reacting a dianhydride, for example, "AC-100," ethylene glycol bistrimellitate dianhydride, manufactured by Chriskev Co. Inc., Leawood, Kans., with a HM/HA, for example, 2-tert-butylaminoethyl methacrylate. This is an example of a hydrophilic monomer that is produced by a reaction in which the dianhydride is reacted with an HM/HA containing a polymerizable group and a secondary amino group on the same molecule, and in which no catalyst is needed for the synthesis reaction. RR is between 1 and 10, HM/HA preferably is 1.55 to less than about 2, and PS, W, and/or F are preferably less than 0.45 moles per mole of dianhydride.

Alternatively, hydrophilic adhesive monomers are produced by reacting a greater number of moles of AC-100 ethylene glycol bistrimellitate dianhydride and/or other dianhydrides with a lesser number of moles of an "F," such as a diamine to form amides and/or imides, and/or diols to form ester intermediates, and at the same time or afterwards, react the residual anhydride groups with HM/HA and other RR compounds.

FORMULATION 18

Other formulations of hydrophilic adhesive polyfunctional monomer intermediates are the reaction products of RR exemplified above with the following dianhydrides: mellophanic dianhydride, bicyclo[2.2.2]octane-2,3,5,6-tetracarboxylic dianhydride; bicyclo[2.2.2]-7-octene-2,3,5,6-tetracarboxylic dianhydride; and other dianhydrides or trianhydrides.

LOW-VISCOSITY COMONOMERS

The viscosities of the reagents used to synthesize the monomers and/or the monomer intermediates and formulations prepared using the hydrophilic adhesive monomers and monomer intermediates described in Formulations 1-18 can be adjusted to optimum levels by mixing the reagents with water-miscible methacrylate or acrylate monomers or other monomers of low viscosity. Useful methacrylate or acrylate monomers include:

Polyethylene Glycol 400 Dimethacrylate; Polyethylene Glycol 600 Dimethacrylate; Polyethylene Glycol 400 Diacrylate, all these manufactured by Scientific Polymer Products, Inc., Ontario, N.Y.; PEG 1,000 Dimethacrylate manufactured by Polysciences, Inc., Warrington, Pa.; polypropylene glycol dimethacrylate; triethylene glycol diacrylate; and low-viscosity liquid glycol monomethacrylates, polyethylene glycol monomethacrylates, oligopropylene glycol monomethacrylates, glycerol dimethacrylate, and other HA/HM compounds. Dimethacrylates are preferred.

POLYMERIZATION INITIATORS

The surface-active polymerization initiators of this invention can adsorb densely on the substrate surface and within the substrate, and can be induced by the action of mobile sensitizers, coreactants, or by the influence of photons to become initiation sites from which the vinyl groups of monomers can polymerize "outward." As a result, the density of the linkages is much higher, restricted only by the dimensions of the chains growing outward from the initiation sites of densely packed surface-bound initiator molecules.

Preferred surface-active polymerization initiators of this invention include the following specific formulations and other related compounds by analogy: The reaction product of 3-quinuclidinol with anhydride compounds; 2-quinuclidine carboxylic acid, other tertiary amines containing a carboxyl group on the same molecule, and other surface-active tertiary amines. The foregoing amines are preferably used in conjunction with adequately hydrophilic photosensitizers and/or peroxides.

For use in the above formulations, nonpolymerizable hydrophilic surface-active polymerization cophotoinitiators are formed when the dianhydride is reacted with a PC type of RR in the absence of a HM/HA; the preferred range is 1.55 to 1.99 moles of PC per mole of dianhydride, optionally with a sum of 0.45 to 0.01 mole of PS, W, and/or F functional moieties. Likewise, PA can be used instead of PC, as in example 2, below. PA derivatives can usually serve also as cophotoiniators.

Surface-active polymerization initiators may also include photosensitive surface-active molecules that can be excited by photons to produce a triplet electronic state capable of adding to vinyl double-bond monomeric groups and/or reacting with tertiary amines, or with other compounds containing abstractable hydrogen atoms, thereby producing free radicals capable of initiating polymerization. Additional Example 2, below, describes the synthesis of one such compound.

Preferred surface-active photoinitiators include camphorquinone sulfonic acid, the reaction product of one mole of BTDA with 1.55 to 1.99 moles of 2-dimethylaminoethanol, camphorquinone oxime addition reaction products with compounds yielding molecules with residual hydrophilicity (most preferably carboxyl surface-active groups), and conjugated ketones and derivatives of camphorquinone containing carboxyl groups attached to one or more sites that do not interfere with the photosensitive nature of the ketone moiety or moieties of the molecules.

Hydrophilic camphorquinone derivatives, analogues, compounds and/or complexes that form triplet, electronically excited states when activated by visible light, and/or amine-peroxide systems are preferred initiators for use in dental and medical applications. For industrial applications, hydrophilic benzophenone-type UV photosensitizing derivatives, surface-active and/or hydrophilic peroxides and/or other initiators (e.g., AIBN [2,2'-azobisisobutyronitrile] and/or its complexes or derivatives) that initiate polymerization by heating, etc., may also be used.

The invention includes the use, in combination with the aforementioned hydrophilic monomers, of free-radical polymerization photoinitiators that are water soluble, or that are attached to some or all of the hydrophilic monomers so that they migrate and penetrate aqueous and hydrophilic environments along with the monomers. The photoinitiators can act in conjunction with amine catalysts used in the synthesis and/or added later. The amine catalysts that are independent or become moieties of the monomers can serve as free-radical polymerization cophotoinitiators.

The most preferred hydrophilic photoinitiators have ionizable groups or surface-active groups or moieties that allow the hydrophilic photoinitiators to bond with the external and internal surfaces of the substrates of interest, imparting enhanced adhesive bonding characteristics to the formulations by virtue of initiation of polymer chain growth from molecules already attached to the substrate. This mechanism decreases steric hindrance limitations and increases the probable density of covalent bonding of surface-active adhesion-promoting coupling agents (attached to substrate) to the overlying polymer. Preferred photoinitiators of this type include camphorquinone-10-sulfonic acid and reaction products of BTDA with RR as exemplified in Formulations 15, 16, and elsewhere herein. Specifically, one mole of BTDA reacted with 1.55 to 1.99 moles of a HM/HA plus 0.45 to 0.01 mole of N,N-dimethylethanolamine yields molecules containing polymerization photoinitiator, cophotoinitiator, and polymerizable moieties all on the same surface-active molecules.

POLYMERIZATION STABILIZERS

The inventive compositions preferably also include a compatible polymerization inhibitor suitable for use during syntheses and storage of the monomers. Specific polymerization inhibitors must be used during the syntheses and storage of the hydrophilic monomers of the present invention. The inhibitors must be of such a nature that their effectiveness will not be lost by reaction with anhydride groups. The inhibitors also need to be sufficiently hydrophilic so they do not become segregated and thereby lose homogeneous distribution in the water-containing hydrophilic formulations. Homogeneous distribution is required to maintain formulation storage stability.

Examples of useful inhibitors and stabilizers include: 4-hydroxymethyl-2,6-di-tert-butylphenol (also known as 4-hydroxy-3,5-di-tert-butylbenzyl alcohol, or as 3,5-di-tert-butyl-4-hydroxybenzyl alcohol), which has a sterically hindered phenolic group that is not subject to reaction with anhydride groups and thus retains its stabilizing activity, is an exemplary PS. 4-Hydroxymethyl-2,6-di-tert-butylphenol has an unhindered primary hydroxyl group that can react with anhydride groups such as those referred to in Formulations 1 to 18 above, to form a preferred stabilizer. Stabilizers are used in very small concentrations in the formulations. Typically the stabilizer concentration ranges from about 0.001% to 1% by weight of the overall monomer formulation.

Other useful stabilizers include 2,5-ditertiary butyl hydroquinone, monotertiary butyl hydroquinone, 3,5-di-t-butyl-4-hydroxy-hydrocinnamate; 4-hydroxy-3,5- di-tert-butylphenyl propionic acid; 3,3'-thiodipropionic acid; 3,5-di-t-butyl-4-hydroxyanisole (2,6-di-t-butyl-4-methoxyphenol); p-benzoquinone; the monomethyl ether of hydroquinone, and hydroquinone.

A particularly interesting stabilizer, which can simultaneously serve as a catalyst for the syntheses of the monomers and also later serve as a coreactant with polymerization photoinitiators, is 2,6-di-tert-butyl-4-(dimethylamino)methylphenol.

REACTIVE DILUENTS

The hydrophilic monomer adhesive composition also may include a reactive diluent. As is shown below, the choice of reactive diluent affects the hydrophilicity of the monomer adhesive composition.

1. Adhesive Monomers with Relatively Low Hydrophilicity

Adhesive monomers with relatively low hydrophilicity are typically a combination of the products of the condensation reaction of 4,8-bis(hydroxymethyl)tricyclo[5.2.1.0$^{2,6}$]decane, also known as tricyclo[5.2.1.0$^{2,6}$]-decane-4,8-dimethanol, with methacrylic anhydride, methacryloyl chloride, acryloyl chloride, and/or acrylic anhydride, which has been previously reacted with dianhydrides comprising those named in Formulations 1-18. Although the molar ratio of 4,8-bis(hydroxymethyl)tricyclo[5.2.1.0$^{2,6}$]decane to these anhydrides or acid chlorides can be varied, the preferred ration is one mole of 4,8-bis(hydroxymethyl)tricyclo[5.2.1.0$^{2,6}$]-decane reacted with one mole of methacrylic anhydride or methacryloyl chloride. Condensation by-products are removed from the reaction products after which the reaction products are reacted with 0.5 mole of a dianhydride selected from those named in Formulations 1-18, preferably those named in Formulations 1, 3, 6, 8, 11, 12, 13, and 18, to produce a monomer with low hydrophilicity.

Likewise, condensation reaction products of 1,4-dimethylolcyclohexane with methacrylic anhydride, methacryloyl chloride, acryloyl chloride, and acrylic anhydride each alone or in combination, can be reacted with dianhydrides comprising those named in Formulations 1-18 inclusive to yield adhesive monomers with relatively low hydrophilicity. The molar ration of 1,4-dimethylolcyclohexane in comparison to the anhydrides or acid chlorides used in the reaction can be varied. However, the preferred ration is one mole of 1,4-dimethylolcyclohexane reacted with one mole of methacrylic anhydride or methacryloyl chloride. The condensation reaction products, after removal of condensation by-products, are reacted with 0.5 mole of a dianhydride selected from those named in Formulations 1-18, and preferably those named in Formulations 1, 3, 6. 8, 11, 12, 13, and 18, to produce an adhesive monomer with low hydrophilicity.

Adhesive monomers of moderate hydrophilicity comprise the reaction products of glycerol dimethacrylate (2-hydroxy-1,3-methacryloxypropane) HM/HA with the dianhydrides named in Formulations 1-18, preferably with eutectic mixtures of the dianhydrides as described herein and in stoichiometries as provided for optimizing the mixtures of components to catalyze the reactions desired.

Viscosity-controlling reactive diluents, that is, liquid crosslinking monomers of low viscosity that are also low in water miscibility, such as 1,4-butanediol dimethacrylate, neopentyl glycol dimethacrylate, tripropylene glycol. diacrylate, 1,6-hexanediol dimethacrylate, and others alone or in combination, contribute to the relatively low hydrophilicity of the formulations. Preferably, the low viscosity liquid monomers are dimethacrylates.

The low hydrophilicity of these monomer formulations is also influenced by the degree of water solubility of the tertiary amine catalysts, the polymerization photoinitiators, and the polymerization inhibitors and stabilizers. Formulations such as these have relatively low equilibrium water concentrations. For adhesive bonding applications, these formulations are suitable for substrates having relatively low hydrophilicities.

2. Adhesive Monomers with Relatively High Hydrophilicity

Highly water-soluble, adhesive, highly crosslinking monomers can be prepared from the reaction of one mole of 3,3',4,4'-diphenylsulfone tetracarboxylic dianhydride or 1,2,3,4-cyclopentanetetracarboxylic dianhydride with 1.55 to 1.8 moles of polyethyleneglycol monomethacrylates or acrylates:

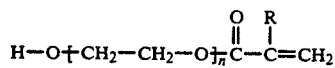

where R is CH$_3$ or H, preferably CH$_3$, and n averages about 2 to 20, preferably about 5 to 10. Hydrolysis of residual anhydride groups after synthesis of the monomers increases the average number of carboxyl groups for the collective monomers in the mixture and, therefore, increases the hydrophilicity and potential for chemical interactions with substrates. After hydrolysis of residual anhydride groups, water-miscible low-viscosity reactive monomer diluents such as ethyleneglycol monomethacrylate, polyethyleneglycol monomethacrylates, Polyethylene Glycol 600 Dimethacrylate, Polyethylene Glycol 400 Diacrylate, PEG 1,000 Dimethacrylate, and glycerol monomethacrylate and glycerol dimethacrylate alone or in combination, can be added to improve the hydrophilicity of the formulations. Preferably the viscosity-controlling reactive diluents are dimethacrylates.

Increased hydrophilicity of monomer formulations is also influenced by the degree of water solubility of the tertiary amine catalysts, the polymerization photoinitiators, and the polymerization inhibitors and stabilizers. The addition of water to a formulation of these ingredients will increase its similitude to biological tissues in vivo.

the nature of these hydrophilic adhesive monomer compositions are such that fluoride-releasing or medicament compounds can be incorporated into the compositions. The water contained in the monomers and/or their polymers provides for the slow release of fluoride ions as desired in dental restorative or caries-preventive materials. Useful fluoride-releasing compounds or medicaments must be somewhat soluble in water. Medicament compounds are restricted to those that are not adversely affected by the free-radical polymerization process. The fluoride-releasing compound can be part of the monomer or polymer structure, or it may be independent of the monomer or polymer structure. When the fluoride-releasing compound is independent of the monomer or polymer structure, it is preferred that the fluoride-releasing compound be physically encompassed by or electronically associated with monomer or polymer constituents.

Examples of suitable fluoride releasing compounds include boron trifluoride in a complex with an amine in the composition, calcium fluoride, fluorosilicates, and the like.

The hydrophilic adhesive monomers of this invention are most useful when available in a kit. The kit preferably includes an air permeable container, for example, a plastic vial, in which the hydrophilic adhesive monomer compositions are stored. The presence of air or oxygen and a polymerization inhibitor inhibits the polymerization of the hydrophilic adhesive monomer composition until the composition is exposed to chemical, thermal, or photopolymerization initiation sources. The source that is used for the initiation of polymerization will, of course, depend upon the polymerization initiators utilized in the hydrophilic adhesive monomer composition, and on the particular adhesive application.

By storing the hydrophilic adhesive monomer composition in an air permeable container there are a number of ways in which the adhesive monomer composition of this invention may be applied to a substrate. First, a polymerization initiator is either mixed with the hydrophilic adhesive monomer composition to give an activated adhesive monomer composition that is applied to the substrate surface, or the polymerization initiator can first be applied to the substrate surface and the hydrophilic adhesive monomer composition subsequently applied to the substrate. Preferred polymerization initiators include lithium toluene-4-sulfinate, stable aromatic sulfinate salts, sulfinic acid derivatives, sulfinic acids, other sulfinate salts, mixtures, or solutions thereof. These preferred compounds and other useful polymerization initiators promote crosslinking during the polymerization of the adhesive monomer composition. Polymerization should not occur until the hydrophilic adhesive monomer composition is located on and has infiltrated into the substrate surface in conjunction with the polymerization initiator(s). Also, polymerization may be initiated by various methods including photoinitiation using a ultra-violet light or a dental blue light, thermal initiation by heat or any other method known in the art, preferably utilizing the various compounds described herein.

ADDITIONAL EXAMPLES

Additional Example 1

A very hydrophilic monomer was produced by heating 139.61 g of Epiclon B4400 in vacuo overnight, and adding it to 290.90 g of Sipomer HEM-5, 0.6 grams of 4-hydroxy-3,5-di-t-butylbenzyl alcohol, and 4.3 grams of methenamine (hexamethylenetetramine) in a glass reaction flask. The mixture was mechanically stirred for about 24 hours at room temperature (about 23° C.). NMR analysis indicated that the reaction was essentially complete and the desired monomeric product was obtained. The viscous liquid product had an $n_D^{22} = 1.491$. The supernatant solution had an osmolality of about 500 mOsm/kg when the monomer was equilibrated with an equal volume of water for 13 days at 21° C.; the resin-rich phase contained about 30 wt. % water, indicating significant hydrophilicity. Camphorquinone was added to the monomer and the mixture polymerized rapidly when photoinitiated with a dental light (blue visible light). The mixture also polymerized rapidly when activated with benzoyl peroxide and 4-(dimethylamino)phenethyl alcohol.

It was surprisingly discovered that the presence of water in this adhesive monomer greatly increased the effective interaction with lithium toluene-4-sulfinate to effect polymerization. It is postulated that water in hydrophilic monomers, such as disclosed herein, facilitates the conversion of stable aromatic sulfinate salts to their unstable sulfinic acid derivatives in the presence of the excess carboxyl groups of the monomers. Sulfinic acids react by oxidation to produce reactive free radicals to promote crosslinked polymerization. Other sulfinate salts would likewise be especially useful for the polymerization and adhesive bonding of formulations comprising monomers such as described in this and the foregoing formulations 1–18. Sulfinate salts and/or their solutions can be applied to the substrate surface before the application of the monomers to the substrate. A lithium paratoluenesulfinate solution applied to dentin surfaces significantly improved the adhesive bond strength when this monomer was used in a bonding formulation. Alternatively, sulfinate salts can be mixed with said monomer formulations just before polymerization and/or bonding is desired.

Additional Example 2

A surface-active tertiary aromatic amine polymerization accelerator, photoinitiator, and cophotoinitiator is produced in this example. The tertiary aromatic amine may be used in the invention as a catalyst for the synthesis of the hydrophilic adhesive monomers, as a polymerization accelerator in the presence of at least one peroxide, and as a polymerization photoinitiator and a cophotoinitiator of vinyl monomers when excited by the absorption of appropriate photons. The tertiary aromatic amine was synthesized by combining 1.9 moles of 4-(dimethylamino)phenethyl alcohol per mole of BTDA (3,3',4,4'-benzophenone tetracarboxylic dianhydride) with stirring and heating.

The same tertiary aromatic amine component product was prepared in refluxing tetrahydrofuran (THF). The progress of the self-catalyzed reaction, which was complete by 32 hours, was monitored via proton NMR spectroscopy. The very viscous liquid product was most soluble (miscible) in liquids having solubility parameters in the range of 9–13 units.

The tertiary aromatic amine catalyzed a polymerization reaction when methacrylate monomers containing the product were exposed to near-ultraviolet photons, or were combined with benzoyl peroxide, at room temperature. Polymerization took place within 10 seconds at room temperature when the product was mixed with a dimethacrylate and camphorquinone and activated with a dental-curing (blue visible) light. Without the tertiary aromatic amine product, at least 30 seconds was required for polymerization of the same methacrylate monomers to occur.

Additional Example 3

A moderately hydrophilic liquid monomer formulation was prepared by reacting one mole of pyromellitic dianhydride with 2.2 moles of hydroxypropyl methacrylate (HPMA, an HM/HA) in the presence of 0.1 wt % of an antioxidant ("Ionox 201"; Shell Chem. Co.), 0.1 wt % di-t-butyl sulfide (as a stabilizer), and 8.1 ml pyridine (as a reaction catalyst) promoted by stirring in the presence of air at 80° C. for one hour. The viscous reaction product was thinned with acetone and washed (extracted) three times with water and one time with n-pentane to remove pyridine and excess HPMA. The fugitive solvents n-pentane and acetone and some of the water were removed by evaporation until the refractive index was about $n_D^{24} = 1.5$ for the clear, light yellow liquid with a sweet, aromatic door. When this product was used in adhesion tests of the kind described in U.S. Pat. Nos. 4,514,527; 4,521,550; 4,588,756; and 4,659,751, the bond strengths to human dentin averaged 1,410 psi.

It has surprisingly been discovered that compounds containing both a polymerization photoinitiator and/or co-photoinitiator and/or a polymerization inhibitor (stabilizer) and/or a polymerizable group can be prepared by using compounds such as those in the foregoing formulations together with the probability statistics described above, provided that during preparation and storage before use, said compounds are protected from high-energy light, contain stabilizers, and are kept under conditions, such as in plastic containers, where they are not deprived of oxygen.

Additional Example 4

A hydrophilic monomer formulation was prepared by combining 1 mole of pyromellitic dianhydride, with 1.9 moles of glycerol dimethacrylate, GDM, a HM/HA, and a trace of stabilizer, PS, using insoluble poly(vinylpyridine) as a catalyst, at room temperature in dried acetone. When NMR showed apparent depletion of the dianhydride, water was admitted inadvertently, hydrolyzing residual anhydride groups. The catalyst was removed by filtration and the acetone was removed by evaporation. Surprisingly, final NMR analysis indicated a monomeric mixture containing a major proportion of molecules containing 3 carboxyl groups, with 2 methacrylate groups, a minor proportion containing 2 carboxyl groups with 4 methacrylate groups, some residual GDM, and little if any pyromellitic acid. Formulations containing this reaction product gave high tensile adhesive bond strengths to prepared dentin and metallic surfaces.

It should be understood that the foregoing disclosure emphasizes certain specific embodiments of the invention and that all modifications or alternatives equivalent thereto are within the spirit or scope of the invention as set forth in the appended claims.

What is claimed is:

1. A hydrophilic fluid crosslinking adhesive composition comprising reaction products of
   (a) a dianhydride with
   (b) a hydrophilic polymerizable monomer compound containing a polymerizable moiety and a reactive group selected from the group consisting of a hydroxyl group, a primary amino group and a secondary amino group; and with
   (c) a reactive reagent selected from the group consisting of compounds containing a reactive group selected from the group consisting of a hydroxyl group, a primary amino group and a secondary amino group; and also containing a functional group selected from the group consisting of (a) one or more compounds containing one reactive hydroxyl group, or primary or secondary amino group, a cophotoinitiator functionality, a polymerization accelerator functionality, and a polymerization stabilizer functionality,
wherein the compounds of subparts (a), (b) and (c) are reacted in molar ratios of about 1:1.55–1.99:0.01–0.45, respectively, to provide the reaction products, and wherein the reaction products have similar aqueous solubility and surface activity characteristics.

2. A composition as in claim 1 wherein the dianhydride of subpart (a) comprises a eutectic mixture of dianhydrides.

3. A composition as in claim 1 wherein the dianhydride of subpart (a) is selected from the group consisting of s-biphenyl tetracarboxylic acid dianhydride, glycerol acetate bistrimellitate dianhydride, 3,3',4,4'-diphenylsulfone tetracarboxylic acid dianhydride, 4,4'-oxydiphthalic dianhydride, 4,4'-(hexafluoroisopropylidene)-bisphthalic anhydride, pyromellitic dianhydride, 3,3',4,4'-benzophenone tetracarboxylic dianhydride, ethylene glycol bistrimellitate dianhydride, 5-(2,5-dioxotetrahydro-3-furanyl)-3-cyclohexene-1,2-dicarboxylic anhydride, 1,2,3,4-cyclopentane tetracarboxylic acid dianhydride, mellophanic dianhydride, bicyclo(2,2,-2)octane-2,3,5,6-tetracarboxylic dianhydride, bicyclo(2,2,2)-7-octene-2,3,5,6-tetracarboxylic dianhydride, and mixtures thereof.

4. A composition as in claim 1 wherein the solubility of the composition in water is at least 1%.

5. A composition as in claim 2 wherein the dianhydride of subpart (a) is selected from the group consisting of s-biphenyl tetracarboxylic acid dianhydride, glycerol acetate bistrimellitate dianhydride, 3,3',4,4'-diphenylsulfone tetracarboxylic acid dianhydride, 4,4'-oxydiphthalic dianhydride, 4,4'-(hexafluoroisopropylidene)-bisphthalic anhydride, pyromellitic dianhydride, 3,3',4,4'-benzophenone tetracarboxylic dianhydride, ethylene glycol bistrimellitate dianhydride, 5-(2,5-dioxotetrahydro-3-furanyl)-3-cyclohexene-1,2-dicarboxylic anhydride, 1,2,3,4-cyclopentane tetracarboxylic acid dianhydride, mellophanic dianhydride, bicyclo(2.2.-2)octane-2,3,5,6-tetracarboxylic dianhydride, bicyclo(2.2.2)-7-octene-2,3,5,6-tetracarboxylic dianhydride, and mixtures thereof.

6. A composition as in claim 1 wherein the polymerizable moiety of the hydrophilic polymerizable monomer compound of subpart (b) is capable of free-radical polymerization.

7. A composition as in claim 1 wherein some of the reaction products contain a polymerizable moiety and a functionality selected from the group consisting of a polymerization cophotoinitiator, a polymerization accelerator and a polymerization stabilizer, located on the same molecule as the polymerizable moiety.

8. A composition as in claim 7 wherein the hydrophilic polymerizable monomer compound of subpart (b) is comprised of molecules that contain a methacrylate or acrylate group connected to a reactive group selected from the group consisting of an unesterified hydroxyl group, a primary amino group and a secondary amino group, said groups connected by a connecting moiety, the connecting moiety selected from the group consisting of —CH$_2$— groups, —CH$_2$CH$_2$O— groups, —CH(CH$_3$)CH$_2$O— groups, —CH(CH$_3$)CH$_2$— groups, cyclic aliphatic groups, heterocyclic aliphatic groups and aromatic groups.

9. A composition as in claim 8 wherein the hydrophilic polymerizable monomer compound of subpart (b) is selected from the group consisting of hydroxymethacrylate, hydroxyacrylate, glycerol dimethacrylate, glycol monomethacrylate, polyethylene glycol monomethacrylate, propylene glycol monomethacrylate, oligopropylene glycol monomethacrylate, hydroxypropyl methacrylate, polypropylene glycol monomethacrylate, hydroxyethyl-methacrylate, glycerol diacrylate, 2-tert-butylaminoethyl methacrylate, the reaction product of methacrylic acid and propylene oxide, and mixtures thereof.

10. A composition as in claim 1 wherein the reaction is catalyzed by a compound selected from the group consisting of an amine-containing catalyst, triphenyl antimony, triphenyl phosphene and mixtures thereof.

11. The composition of claim 1 wherein the cophotoinitiator functionality of the compound of subpart (c) is a tertiary amino group.

12. The composition of claim 11 wherein the same compound comprises the cophotoinitiator functionality and the amine-containing catalyst of the reaction.

13. The composition of claim 1 wherein the hydrophilic polymerizable monomer compound of subpart (b) is 2-tert-butylaminoethyl methacrylate.

14. A composition as in claim 1 wherein the reaction products comprising the composition have similar aqueous solubility and surface activity characteristics.

15. The composition of claim 1 wherein the aqueous solubility characteristic of the reaction products comprising the composition is low hydrophilicity.

16. The composition of claim 15 wherein the composition comprises the reaction product of 4,8-bis(hydroxymethyl)tricyclo(5.2.1.0$^{2,6}$)decane with a compound selected from the group consisting of methacrylic anhydride, methacryloyl chloride, acryloyl chloride, acrylic anhydride and mixtures thereof.

17. The composition of claim 14 wherein the composition comprises the reaction product of 1,4-dimethylcyclohexane with a compound selected from the group consisting of methacrylic anhydride, methacryloyl chloride, acryloyl chloride, acrylic anhydride, and mixtures thereof.

18. The composition of claim 1 wherein the aqueous solubility characteristic of the compounds comprising the composition is moderate hydrophilicity.

19. The composition of claim 18 wherein the hydrophilic polymerizable monomer compound of subpart (b) is glycerol dimethacrylate.

20. The composition of claim 1 wherein the aqueous solubility characteristic of the compounds comprising the composition is high hydrophilicity.

21. The composition of claim 20 wherein the hydrophilic polymerizable monomer compound of subpart (b) is polyethylene glycol mono(meth)acrylate.

22. The composition of claim 21 wherein the dianhydride of subpart (a) is selected from the group consisting of 3,3',4,4'-diphenylsulfone tetracarboxylic acid dianhydride and 1,2,3,4-cyclopentane tetracarboxylic acid dianhydride.

23. The article of manufacture of claim 21 wherein the ratio of moles of the compounds of subpart (b) to the dianhydride of subpart (a) is at least 2:1, and the aqueous solubility characteristics of the compounds comprising the composition is high hydrophilicity.

24. The composition of claim 14 wherein the composition is isotonic with normal saline.

25. A dental adhesive comprising the composition of claim 1.

26. A dental adhesive according to claim 25 wherein the composition comprises the reaction product of hydroxyethylmethacrylate and a eutectic mixture of s-biphenyl tetracarboxylic acid dianhydride and pyromellitic dianhydride.

27. A dental adhesive according to claim 25 that is comprised of the reaction products of pyromellitic dianhydride, hydroxypropyl methacrylate, pyridine and di-tert-butyl sulfide.

28. A dental adhesive according to claim 25 that is comprised of the reaction products of pyromellitic dianhydride, glycerol dimethacrylate and poly(vinylpyridine).

29. The dental adhesive of claim 25 also containing medicaments, wherein the medicaments are fluoride-containing compounds.

30. The dental adhesive of claim 29 wherein the fluoride-containing compounds are selected from the group consisting of boron trifluoride in an amine-containing complex, calcium fluoride and fluorosilicates.

31. A tissue adhesive comprising the composition of claim 1.

32. The tissue adhesive of claim 31 wherein the tissue is selected from the group consisting of bone, dentin and enamel.

33. The tissue adhesive of claim 31 also containing medicaments.

34. An industrial adhesive comprising the composition of claim 1.

35. A polymerized hydrophilic adhesive composition comprising the composition of claim 1 and a polymerization initiator.

36. The polymerized hydrophilic adhesive composition of claim 35 wherein the polymerization initiator is selected from the group consisting of an amine-peroxide catalyst, an alkali metal salt of a sulfinate and a derivative of camphorquinone.

37. A method of making a hydrophilic fluid crosslinking adhesive composition comprising the steps of reacting
  (a) a dianhydride with
  (b) a hydrophilic polymerizable monomer compound containing a polymerizable moiety and a reactive group selected from the group consisting of a hydroxyl group, a primary amino group and a secondary amino group; and with
  (c) a reactive reagent selected from the group consisting of compounds containing a reactive group selected from the group consisting of a hydroxyl group, a primary amino group and a secondary amino group; and also containing a functional group selected from the group consisting of a cophotoinitiator functionality, a polymerization accelerator, and a polymerization stabilizer functionality and water, the reaction promoted by heat in the presence of a catalyst, wherein the reaction products have similar aqueous solubility and surface activity characteristics.

38. The method of claim 37 wherein there are from about 1.5 to less than about 2 moles of the hydrophilic polymerizable monomer compound of subpart (b) per mole of dianhydride, and catalysts are selected from the group consisting of an amine, triphenyl antimony, triphenyl phosphene and mixtures thereof.

39. A method for preparing the surface of dentin, enamel, bone, or other natural or industrial substrates for adhesion of composite material and resins, the method comprising:
  (a) applying a polymerization initiator to the substrate;
  (b) applying the composition of claim 1 to the substrate; and
  (c) reacting the mixture under conditions and for time sufficient for polymerization to occur.

40. The method of claim 39 wherein the composition of claim 1 and the polymerization initiator are first prepared as a mixture and the mixture applied to the substrate.

41. The method of claim 39 wherein the polymerization initiator is selected from the group consisting of an amine-peroxide catalyst, an alkali metal salt of a sulfinate and a derivative of camphorquinone.

42. The method of claim 39 wherein the conditions of polymerization are selected from the group consisting of heating and illumination with visible or ultraviolet light.

43. An article of manufacture comprising
   (1) a first container containing a hydrophilic fluid crosslinking adhesive composition comprising
      (a) reaction products of a dianhydride with a hydrophilic polymerizable monomer compound containing a polymerizable moiety and a reactive group selected from the group consisting of a hydroxyl group, a primary amino group and a secondary amino group; and
      (b) a reactive reagent selected from the group consisting of compounds containing a reactive group selected from the group consisting of a hydroxyl group, a primary amino group and a secondary amino group; and also containing a functional group selected from the group consisting of a cophotoinitiator functionality, a polymerization accelerator, and a polymerization stabilizer functionality, wherein the reaction products have similar aqueous solubility and surface activity characteristics; and
   (2) a second container containing a polymerization initiator.

44. The article of manufacture of claim 43 wherein there are from about 1.5 to less than about 2 moles of the hydrophilic polymerizable monomer compound of subpart (a) per mole of dianhydride.

45. The article of manufacture of claim 43 wherein the first container is air-permeable.

46. The article of manufacture of claim 43 wherein the first container also contains a polymerization inhibitor.

47. The article of manufacture of claim 46 wherein the polymerization inhibitor contains an aromatic, sterically-hindered hydroxyl group.

48. The article of manufacture of claim 43 wherein the hydrophilic fluid adhesive composition is a dental adhesive.

49. The article of manufacture of claim 48 wherein the dental adhesive also contains medicaments.

50. The article of manufacture of claim 43 wherein the hydrophilic fluid adhesive composition is an industrial adhesive.

51. A hydrophilic fluid crosslinking adhesive composition produced by the process of reacting
   (a) a dianhydride with
   (b) a hydrophilic polymerizable monomer compound containing a polymerizable moiety and a reactive group selected from the group consisting of a hydroxyl group, a primary amino group and a secondary amino group; and with
   (c) a reactive reagent selected from the group consisting of compounds containing a reactive group selected from the group consisting of a hydroxyl group, a primary amino group and a secondary amino group; and also containing a functional group selected from the group consisting of a cophotoinitiator functionality, a polymerization accelerator, and a polymerization stabilizer functionality; and
   (d) water,
the reaction catalyzed by heating or by a catalyst selected from the group consisting of an amine-containing catalyst, triphenyl antimony, triphenyl phosphene and mixtures thereof, wherein the reaction products have similar aqueous solubility and surface activity characteristics.

52. A hydrophilic fluid crosslinking adhesive composition produced by the process of claim 51 wherein there are from about 1.5 to less than about 2 moles of the hydrophilic polymerizable monomer compound of subpart (b) per mole of dianhydride.

53. The composition of claim 7 wherein the polymerizable moiety is a methacrylate, an acrylate or a vinyl moiety.

54. A composition as in claim 52 wherein there are from about 1.55 to about 1.99 moles of the compounds of subpart (b), and from about 0.01 to about 0.45 moles of the compounds of subpart (c), per mole of the compounds of subpart (a).

55. A composition as in claim 1 wherein the reactive reagent of subpart (c) is selected from the group consisting of 3,5-di-tert-butyl-4-hydroxybenzyl alcohol, mono-tert-butylhydroquinone and hydroquinone.

56. A composition as in claim 1 wherein the hydrophilic polymerizable monomer compound of subpart (b) is polyethyleneglycol monomethacrylate.

57. A hydrophilic fluid crosslinking adhesive composition comprising water and reaction products of:
   (a) a dianhydride with
   (b) a hydrophilic polymerizable monomer compound containing a polymerizable moiety and a reactive group selected from the group consisting of a hydroxyl group, a primary amino group and a secondary amino group; and also a compound containing a functional group selected from the group consisting of a cophotoinitiator functionality, a polymerization accelerator functionality, and a polymerization stabilizer functionality,
wherein the compounds of subparts (a) and (b) are present in the composition in molar ratios of about 1:1.55–1.99, and wherein the reaction products have similar aqueous solubility and surface activity characteristics.

* * * * *